United States Patent [19]

Ginn

[11] Patent Number: 5,540,236
[45] Date of Patent: Jul. 30, 1996

[54] GUIDE WIRE EXIT PORT

[75] Inventor: Richard S. Ginn, San Jose, Calif.

[73] Assignee: Cardiovascular Imaging Systems, Incorporated, Sunnyvale, Calif.

[21] Appl. No.: 286,296

[22] Filed: Aug. 5, 1994

[51] Int. Cl.⁶ ...................................................... A61B 5/00
[52] U.S. Cl. .............................................................. 128/772
[58] Field of Search .................................. 128/657, 658, 128/772; 604/95, 164, 270–272

[56] References Cited

U.S. PATENT DOCUMENTS

| | | | |
|---|---|---|---|
| 4,552,554 | 11/1985 | Gould et al. | 604/51 |
| 4,824,435 | 4/1989 | Giesy et al. | 604/49 |
| 4,932,413 | 6/1990 | Shockey et al. | 128/657 |
| 4,951,677 | 8/1990 | Crowley et al. | 128/662.06 |
| 5,024,234 | 6/1991 | Leary et al. | 128/663.01 |
| 5,201,316 | 4/1993 | Pomeranz et al. | 128/662.06 |
| 5,203,338 | 4/1993 | Jang | 128/662.06 |
| 5,219,335 | 6/1993 | Willard et al. | 604/164 |
| B1 4,762,129 | 7/1991 | Bonzel | 606/194 |

FOREIGN PATENT DOCUMENTS

| | | |
|---|---|---|
| 07323 | 2/1994 | WIPO . |
| 07217 | 2/1994 | WIPO . |

*Primary Examiner*—Max Hindenburg
*Attorney, Agent, or Firm*—Townsend and Townsend and Crew LLP

[57] ABSTRACT

A catheter is provided having a catheter body with a proximal end, a distal end, and a central axis therebetween. A guide wire lumen is provided which terminates in a channel which is directed laterally outward from the central axis and through the catheter body between the proximal and distal ends. The channel is defined by a pair of opposing walls and a surface therebetween which is inclined radially outward from the central axis to orient a guide wire in a direction generally aligned with the central axis as it leaves the catheter body.

19 Claims, 8 Drawing Sheets

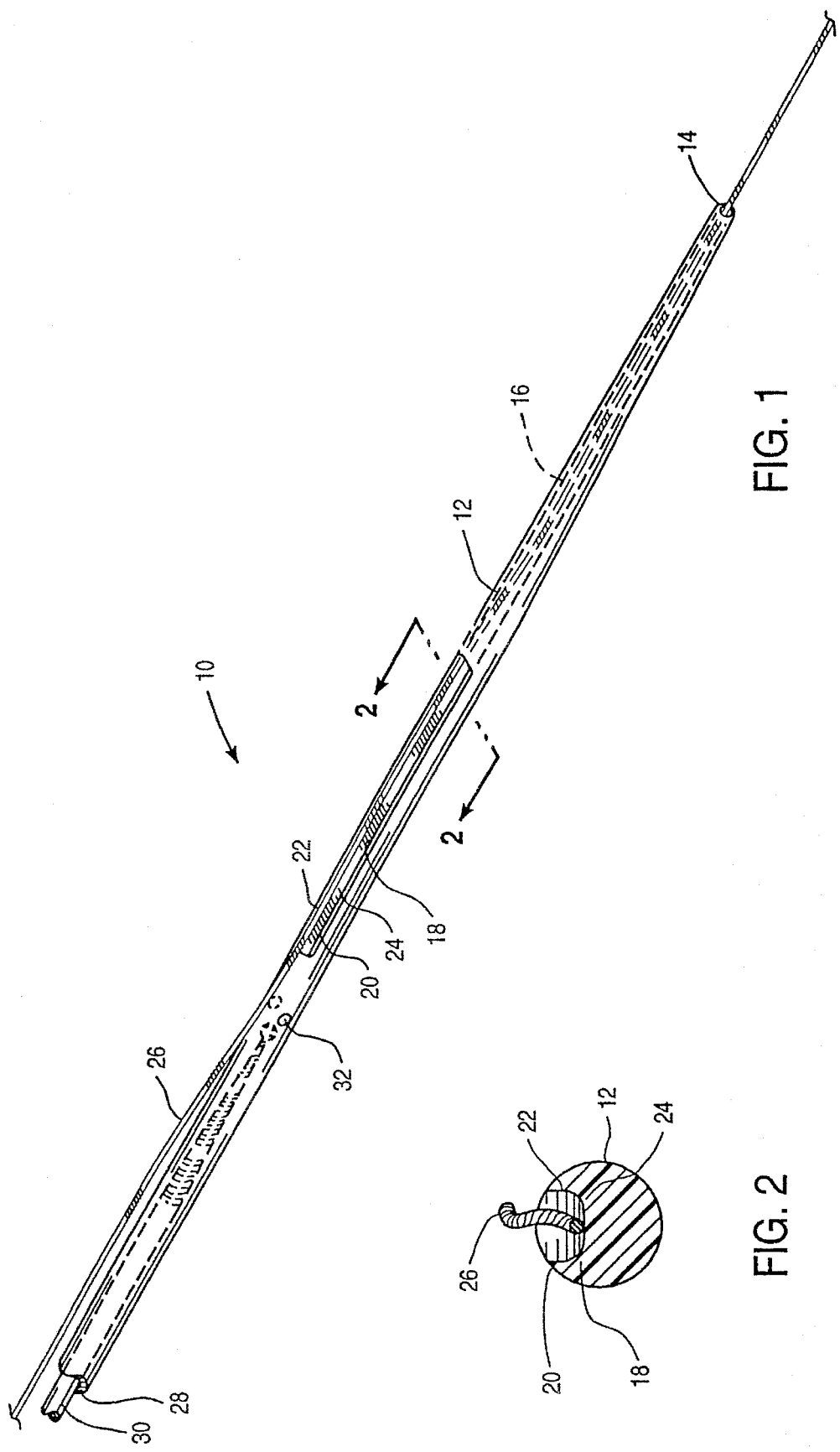

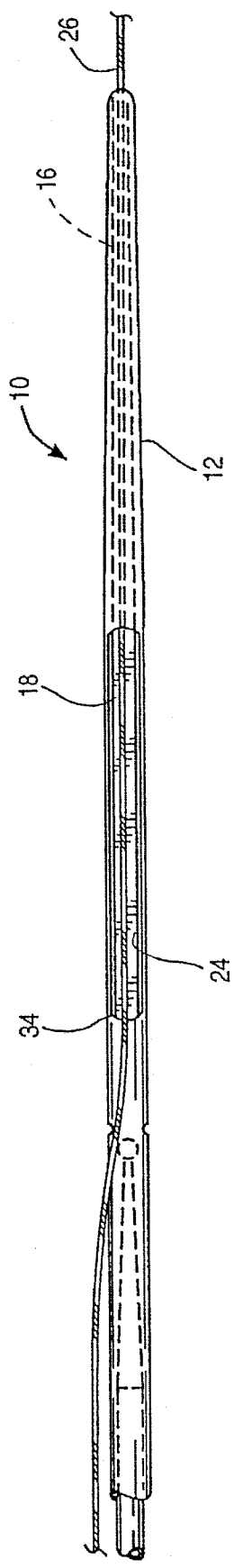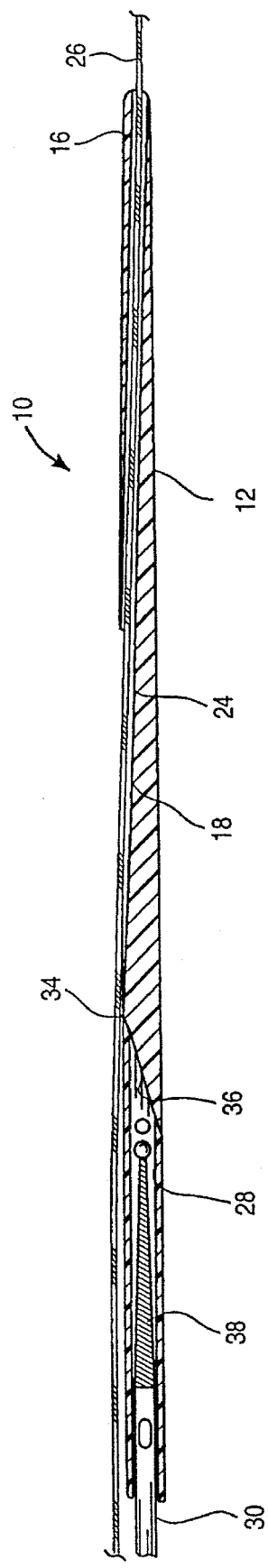

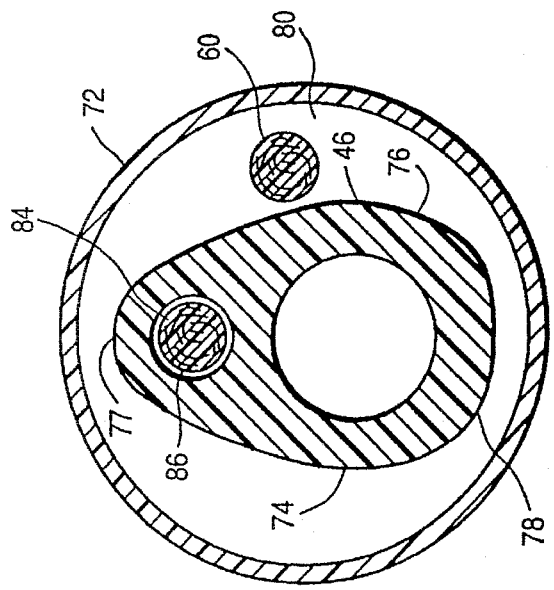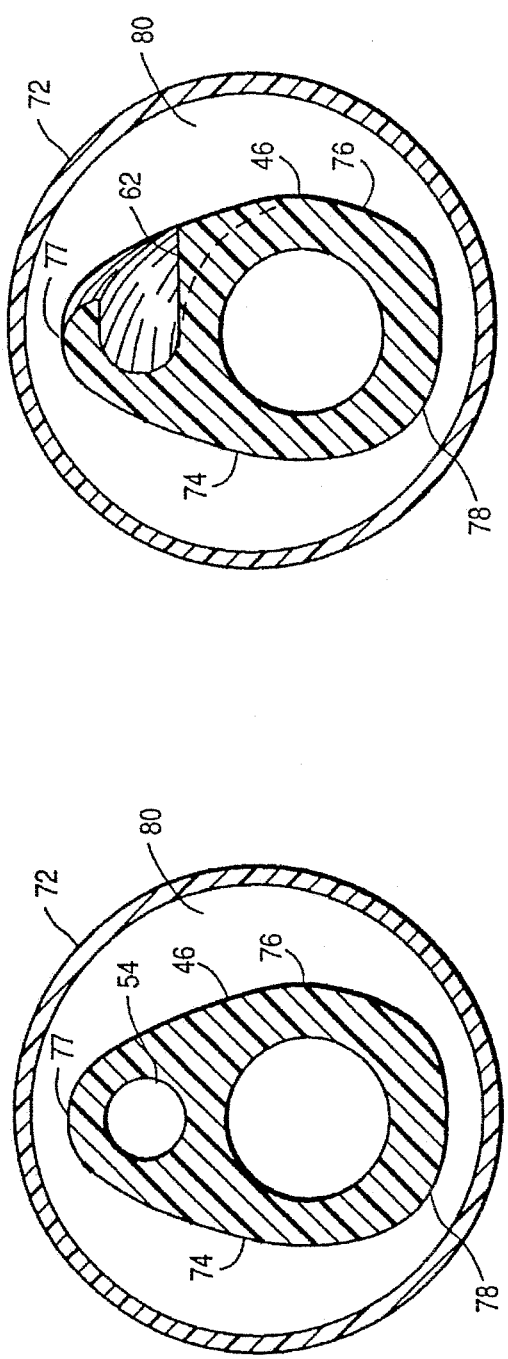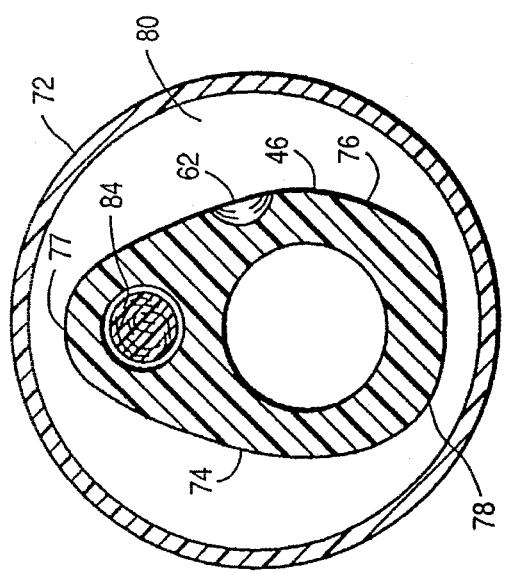
FIG. 8  FIG. 9  FIG. 10  FIG. 11

GUIDE WIRE EXIT PORT

BACKGROUND OF THE INVENTION

1. Field of the Invention

The invention relates generally to vascular catheters, and in particular to improved vascular catheters having guide wire lumens which terminate through the catheter body.

Atherosclerosis is a common human ailment arising from deposition of fatty-like substances, referred to as atheroma, or plaque, on the walls of blood vessels. Such deposits occur within the peripheral blood vessels, which feed the limbs of the body, and the coronary vessel, which feed the heart. When deposits accumulate in localized regions of blood vessels, narrowing of the vascular lumen, referred to as stenosis, occurs. Blood flow is restricted and the person's health is at serious risk.

Numerous approaches for opening such stenosed regions are known. Of particular interest to the present invention are approaches which introduce diagnostic or therapeutic devices into the vascular anatomy through a guiding catheter or a sheath. Insertion of guiding catheters into the heart is described generally in U.S. Pat. No. 5,163,921, the disclosure of which is herein incorporated by reference. Briefly, guiding catheters are typically inserted into the femoral artery in the groin and advanced towards the heart. The guiding catheter is then directed through the patient's aorta until the distal tip of the guiding catheter reaches the ostium of one of the coronary arteries. Once the guiding catheter is placed in the ostium, various therapeutic or diagnostic devices can be inserted through the guiding catheter and into the coronary artery.

In order to introduce the various devices beyond the distal end of the guiding catheter, a guide wire is commonly employed. The guide wire is introduced into the vascular anatomy through the guiding catheter where a distal end of the guide wire is advanced past a distal end of the guiding catheter and into the coronary artery. With the guide wire in place, a diagnostic or therapeutic catheter can be advanced over the guide wire and into the area of interest. Diagnostic or therapeutic catheters of interest include a lumen for receiving the guidewire so that the catheters can be advanced over the guide wire in a manner often referred to as "tracking".

Of particular interest to the present invention are catheters or sheaths where the guide wire lumen terminates through the body of the catheter or sheath between a proximal and a distal end. Unlike previous catheter designs (often referred to as "over the wire" catheters) wherein the guide wire lumen extends the entire length of the catheter body, these catheters have a guide wire lumen which extends only over a portion of the catheter body.

One particular catheter design of interest where the guide wire lumen does not extend the full length of the catheter shaft is the "rapid exchange" catheter design. In rapid exchange catheters, the guide wire exits the catheter shaft at some point near the distal end of the catheter and the remaining length of the guide wire runs alongside the catheter shaft until both the catheter and the guide wire exit the patient.

Two rapid exchange catheter designs which are of particular interest to the present invention are long lumen rapid exchange designs and short lumen rapid exchange designs (the latter sometimes being referred to as "monorail" designs). In the case of long lumen rapid exchange catheters, the side port through which the guide wire exits will typically be 10 cm or more from the distal tip of the catheter. In a particular type of long lumen rapid exchange catheter, referred to as a common lumen rapid exchange catheter (described generally in U.S. Pat. No. 5,203,338, the disclosure of which is herein incorporated by reference), the catheter body includes a working lumen in addition to the guide wire lumen. These two lumens are disposed in a proximal region of the catheter and are in communication with a common lumen at a distal region of the catheter. When inserting the common lumen catheter into a patient, the guide wire is introduced through the common lumen and advanced into the guide wire lumen. The relatively long engagement of the guide wire with the common lumen and the guide wire lumen allows the distal end of the catheter to more easily be passed through tortuous of the regions of the vascular anatomy, i.e. provides good trackability. Once the catheter is in the desired region of the vascular anatomy, the guide wire can be withdrawn from the vessel and stored in the guide wire lumen just proximal to the common lumen. A diagnostic or therapeutic device can then be advanced from the working lumen and into the common lumen without being obstructed by the guide wire.

A particular diagnostic device which is of interest to the present invention is an ultrasonic imaging core that can be advanced form the working lumen and into the common lumen to produce an image concerning the extent and nature of the stenotic material in the vessel. The ultrasonic imaging core will often include an imaging transducer or reflective element mounted on a rotatable drive shaft disposed within a flexible catheter body. The transducer, reflective element, or both, can be rotated within the catheter body to direct an ultrasonic signal generally outward in order to scan the interior of the blood vessel wall.

Short lumen rapid exchange catheter designs generally employ a much shorter guide wire lumen at the distal end of the catheter, typically in the range from about 1 cm to 4 cm. Unlike the long lumen rapid exchange catheters, the guide wire lumen is disposed entirely within the distal region of the catheter body. The short lumen rapid exchange catheter further includes a central lumen extending from a proximal end and terminates near the guide wire lumen. Once the short lumen rapid exchange catheter is positioned within the artery, an interventional, imaging, or diagnostic component of the catheter can be advanced through the access lumen and up to the guide wire lumen.

Other catheters or sheaths having a guide wire lumen which terminates through the catheter body include "convertible tip" catheters and sheaths as described generally in copending U.S. patent application Ser. No. 08/292,864 (Attorney Docket No. 12553-47), filed Jul. 29, 1994, the disclosure of which is herein incorporated by reference, and "rapid exchange delivery catheters" as described generally in copending U.S. patent application Ser. No. 08/271,878 (Attorney Docket No. 12553-48), filed Jul. 7, 1994, the disclosure of which is herein incorporated by reference.

The termination of the guide wire lumen through the side of the catheter body presents particular problems not generally associated with catheters where the guide wire lumen extends the entire length of the catheter body. One particular problem is the transitioning of the exit of the guide wire from the catheter body and into the guiding catheter. As the guide wire exits laterally outward through the catheter body, it is desired to have the guide wire gently redirected toward the catheter body so that the guide wire can run alongside the catheter body without kinking or producing an excessive amount of friction with the catheter body, both of which can reduce trackability.

A particular problem experienced with short lumen rapid exchange catheter designs is buckling or prolapse of the guide wire when the catheter is removed from the vessel. Buckling or prolapse of the guide wire when removing the catheter from the patient can cause serious inconvenience and can be time consuming for a surgeon removing the catheter.

In some common lumen rapid exchange catheter designs, the proximal region of the catheter has an asymmetrical cross section. Such an asymmetrical configuration reduces the catheter profile so that the guide wire can more easily run alongside the catheter as it exits the patient. When the guide wire exits such catheters, it is preferred to have the guide wire follow a single side of the catheter body. One problem experienced with such designs, however, is the spiraling of the guide wire around the catheter body which effectively increases the profile of the catheter and reduces trackability.

It would therefore be desirable to provide catheters and sheaths which improve trackability and reduce the possibility of having the guide wire buckling or prolapse. In the case of asymmetrical catheter designs, it would further be desirable to provide a catheter body wherein the guide wire can exit the catheter body and travel along a single side of the catheter body until exiting the patient.

2. Description of the Background Art

Vascular ultrasonic imaging catheters having rapid exchange designs are described in U.S. Pat. Nos. 5,201,316; 5,204,234; and 4,951,677. Catheter sheaths having guide wire side ports near the distal ends are described in U.S. Pat. Nos. 4,932,413; 4,824,435; and 4,552,554. A short lumen rapid exchange balloon dilation catheter is described in U.S. Pat. No. 4,762,129. An ultrasonic imaging catheter having a common distal lumen is described in U.S. Pat. No. 5,203,338. A catheter having two lumens in a proximal region and a single lumen in a distal region is described in U.S. Pat. No. 5,219,335. A catheter having a guide wire lumen with a slidable sleeve is described in PCT International Application No. PCT/US93/07323 and PCT/US93/07217.

SUMMARY OF THE INVENTION

According to the invention, a vascular catheter is provided having a catheter body with a proximal end, a distal end, and a central axis therebetween. The catheter further includes a guide wire lumen which extends from the distal end and terminates in a channel directed laterally outward from the central axis and through the catheter body between the proximal and distal ends. The channel is defined by a pair of opposing walls and a surface therebetween. The surface is inclined radially outward from the central axis to orient a guide wire in a direction generally aligned with the central axis as it leaves the catheter body. In one particular aspect, the channel extends over a length in the range from about 3 mm to 25 mm and is aligned precisely with the central axis. In another aspect, the channel is spiralled around at least a portion of the catheter body.

In one particular exemplary embodiment, a vascular catheter is provided having a catheter body with a proximal end, a distal end, and a central axis therebetween. A central lumen is generally aligned with the central axis, and extends from the proximal end and terminates near the distal end. A guide wire lumen is provided and extends from the distal end and terminates in a channel directed laterally outward from the central axis and through the catheter body near the termination of the central lumen so that the guide wire lumen is separate from the central lumen. The channel is defined by a pair of opposing walls and a surface therebetween which is inclined radially outward from the central axis. The channel is open to the environment over a length in the range from 3 mm to 25 mm. This configuration allows for a guide wire to be oriented in a direction generally aligned with the central axis as it leaves the catheter body.

Preferably, the surface is inclined at an angle in the range from 5 degrees to 30 degrees relative to the central axis. In another aspect, the channel is aligned precisely with the central axis and is about 1.5 cm to 5 cm from the distal end.

In another exemplary embodiment, a vascular catheter is provided having a catheter body with a proximal end, a distal end, and a central axis therebetween. The catheter body includes a proximal region having at least two lumens and a distal region having a single lumen which is connected to and in communication with both of the lumens in the proximal region. The cross sectional area of the distal region is less than the combined cross sectional area of the two lumens of the proximal region. One of the lumens in the proximal region is a guide wire lumen which extends from the single lumen and which terminates in a channel directed laterally outward from the central axis and through the catheter body between the proximal end and the single lumen. The channel is defined by a pair of opposing walls and a surface therebetween which is inclined radially outward from the central axis. This configuration orients a guide wire in a direction generally aligned with the central axis as it leaves the catheter body. Preferably, the channel is disposed about 20 cm to 30 cm from the distal end.

In a particular aspect, the catheter body at the proximal region has two sides, a top, and a bottom with the top-to-bottom dimension being larger than the side-to-side dimension. The channel is directed to align the guide wire along one of the sides. Preferably, a portion of the channel is spiralled about the catheter body to align the guide wire along the side having the channel. In another aspect, one of the lumens in the proximal region is a working lumen and is disposed between the guide wire lumen and the bottom.

Preferably, the distal region has a length in the range from 10 cm to 20 cm with the channel being disposed near a proximal end of the distal region.

A method is provided for introducing a vascular catheter into an access lumen of a guiding catheter. The method includes inserting a guide wire into the access lumen of the guiding catheter. A proximal end of the guide wire is then inserted into a lumen of the vascular catheter. The vascular catheter is proximally advanced over the guide wire so that the proximal end of the guide wire exits the vascular catheter along a side of the vascular catheter and passes through a channel in the side of the vascular catheter. The channel orients the exit of the guide wire along the side of the vascular catheter.

In one particular aspect of the method, the channel is generally aligned with a central axis of the catheter body, and the channel orients the exit of the guide wire in a direction generally aligned with the central axis. In another aspect, the vascular catheter includes a central lumen disposed between the guide wire lumen and a bottom edge of the vascular catheter. The channel orients the exit of the guide wire from the guide wire lumen toward the bottom edge and then along the side of the vascular catheter in a direction generally aligned with the central axis.

BRIEF DESCRIPTION OF THE DRAWINGS

FIG. 1 illustrates a short lumen rapid exchange catheter design having a channel for orienting a guide wire as it leaves the catheter body according to the present invention.

FIG. 2 is a cross sectional view of FIG. 1 taken along lines 2—2.

FIGS. 3 and 4 illustrate top and side views, respectively, of the catheter of FIG. 1.

FIGS. 8–11 are cross sectional views of the catheter of FIG. 7 taken along lines 8—8, 9—9, 10—10, and 11—11, respectively (with the guide wire being shown only in FIG. 11).

DETAILED DESCRIPTION OF THE SPECIFIC EMBODIMENTS

Figure 5:
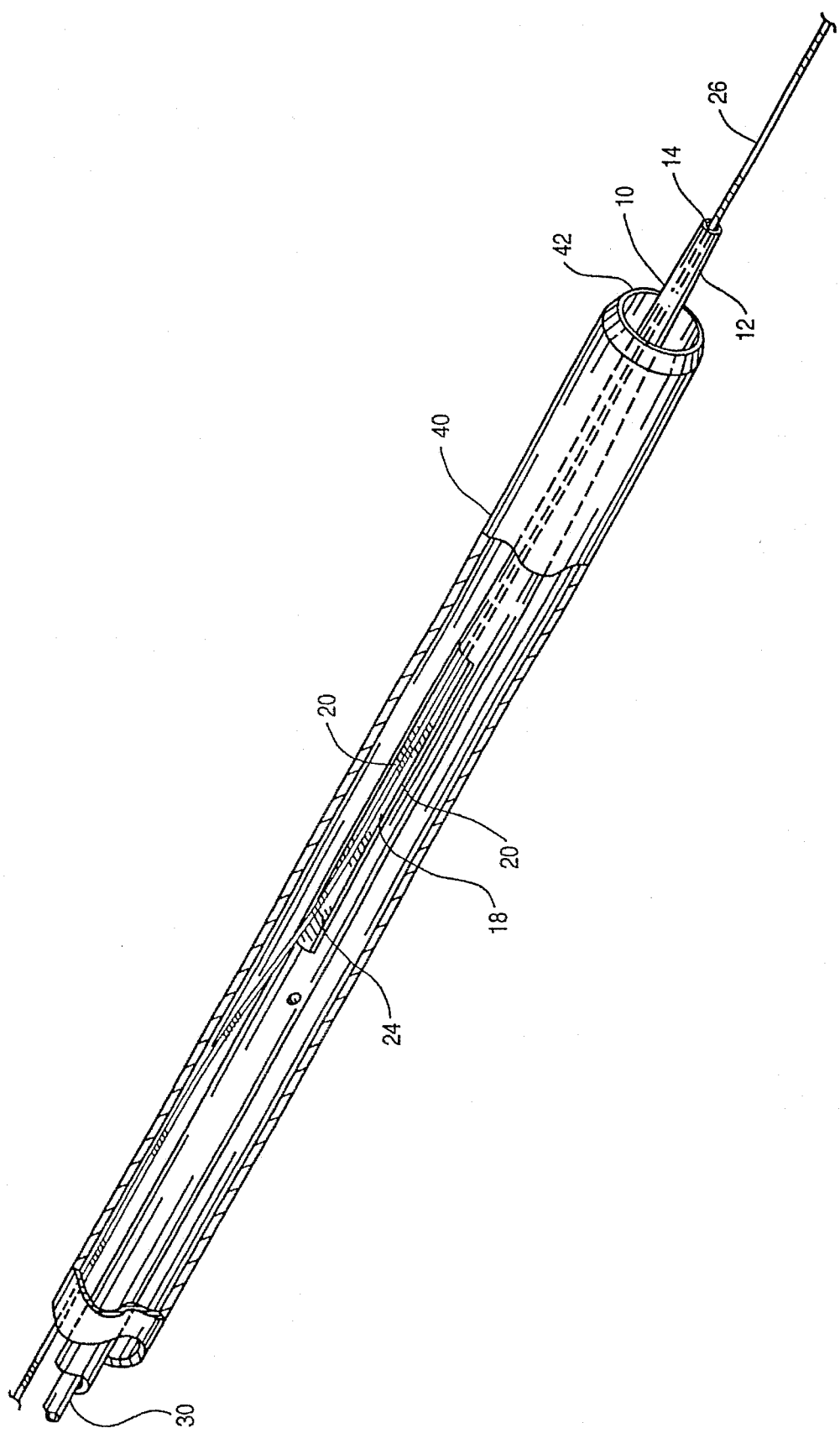
FIG. 5 illustrates the catheter of FIG. 1 within a guiding catheter.

The invention provides a vascular catheter which includes a catheter body having a proximal end, a distal end, and a central axis therebetween. A guide wire lumen which terminates in a channel which extends laterally outward from the central axis and through the catheter body between the proximal and distal ends is also provided. The channel is defined by a pair of opposing walls and a surface therebetween which is inclined radially outward from the central axis to orient a guide wire in a direction generally aligned with the central axis as it leaves the catheter body.

In an exemplary aspect, the vascular catheter is used within a guiding catheter with the channel serving to transition the exit of the guide wire from the catheter body of the vascular catheter, into the guiding catheter, and alongside the body of the vascular catheter. The channel provides a gradual and a smooth transition of the guide wire from the catheter body to enhance trackability and reduce the possibility that the guide wire will kink when the vascular catheter is advanced over the guide wire. The walls of the channel orient the guide wire along the length of the catheter body to reduce the possibility that the guide wire will wrap around the catheter body.

Referring to FIGS. 1 and 2, an exemplary embodiment of a vascular catheter 10 having a short lumen rapid exchange design will be described. The vascular catheter 10 includes a catheter body 12 having a distal end 14 and a proximal end (not shown) with a central axis along the length of the catheter body 12. A guide wire lumen 16 (shown in phantom) is disposed in the catheter body 12 with one end terminating at the distal end 14 and the other end terminating in a channel 18. The channel 18 extends laterally outward from the central axis and through the catheter body 12. The channel 18 is defined by a pair of opposing walls 20, 22 and a surface 24 extending between the walls 20, 22. In a preferable aspect, the cross-sectional geometry of the walls 20, 22 and the surface 24 is U-shaped. The surface 24 is inclined radially outward from the central axis so as to provide a smooth and gradual transition for an exiting guide wire 26 while the walls 20, 22 orient the guide wire 26 along the length of the catheter body 12.

The channel 18 will preferably be located from about 1.5 cm to about 5 cm from the distal end 14, and the length of the channel will preferably be in the range from about 3 mm to 25 mm. Over this length, the channel 18 is open to the environment. The channel 18 will preferably be aligned precisely with the central axis. As described in greater detail hereinafter, the vascular catheter 10 further includes a central lumen 28 for holding a diagnostic or a therapeutic element, such as an ultrasonic imaging core 30. A pair of flush ports 32 can optionally be provided for bleeding air when the imaging core 30 is introduced into the central lumen 28.

Referring to FIGS. 3 and 4, construction of the vascular catheter 10 will be described in greater detail. The channel 18 can best be formed by angling the guide wire lumen 16 from the distal end 14 to where the guide wire lumen 16 exits the catheter body 12 (see FIG. 4). In this manner, the surface 24 of the channel 18 is an extension of the guide wire lumen 16. In a particular aspect, the catheter body 12 is formed as a solid structure at a point 34 near where the channel 18 ends to form a distal end 36 of the central lumen 28. Once the catheter 10 is inserted over the guide wire 26, the imaging core 30 can be advanced through the central lumen 28 until a tracking tip 38 of the imaging core 30 reaches the distal end 36. At this point, the imaging core 30 can be rotated for imaging a stenosed region.

At point 34, the guide wire 26 has completely exited the catheter body 12. The channel 18 provides a smooth and gradual transition from the catheter body 12 so that the guide wire 26 will not bend or kink near point 34 as the guide wire 26 is further directed alongside the catheter body 12. The angle of inclination of the surface 24 can be varied depending on the particular application and the nature of the guide wire 26. Preferably, the surface will be inclined at an angle in the range from 5 degrees to 30 degrees relative to the central axis. The walls 20, 22 orient the guide wire 26 along the catheter body 12 to reduce the possibility that the guide wire 26 will wrap around the catheter body 12 after exiting the channel 18.

Referring to FIG. 5, the vascular catheter 10 is shown within a guiding catheter 40. Before inserting the vascular catheter 10 into the guiding catheter 40, the guiding catheter 40 is first introduced into the vascular anatomy. The guide wire 26 is then advanced through the guiding catheter 40 until it passes beyond a distal tip 42 of the guiding catheter 40 and into a desired vessel. The vascular catheter 10 is then inserted over the guide wire 26 by advancing the distal end 14 of the catheter body 12 over the guide wire 26 until a proximal end (not shown) of the guide wire 26 exits the guide wire lumen 16 and passes through the channel 18. After exiting the channel 18, the guide wire 18 is generally aligned, i.e. substantially parallel with, the central axis of the catheter body 12. Both the opposing walls 20, 22 and the surface 24 assist to orient the guide wire 26 in this manner. The guide wire 26 then passes further through the guiding catheter 40 and alongside the catheter body 12 until exiting the patient. With the guide wire 26 being generally aligned with the central axis, trackability is improved as the vascular catheter 10 is advanced through the guiding catheter 40.

Once the catheter 10 is advanced over the guide wire 26 and into the desired region, the imaging core 30 is rotated to produce a visual image of the stenosed region of the artery while being advanced or pulled back through the central lumen 28 as previously described.

When the vascular catheter 10 is removed from the patient, the channel 18 provides a smooth transition region which helps prevent buckling or prolapse of the guide wire 26. By reducing this possibility, the vascular catheter 10 can more rapidly be removed from the patient.

Figure 6:
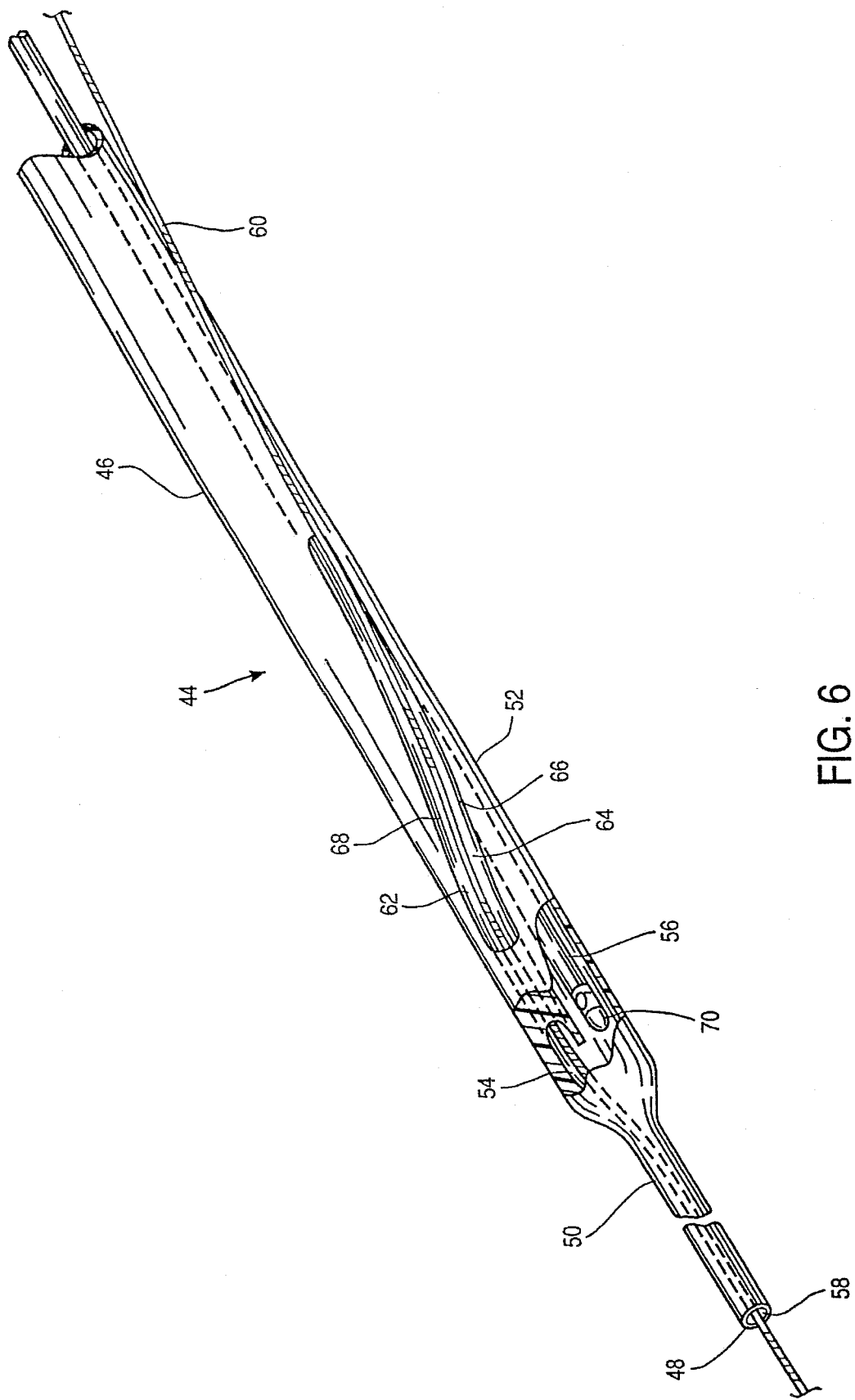
FIG. 6 illustrates a catheter having a long lumen rapid exchange catheter design and having a curved channel for orienting the exit of a guide wire according to the present invention.

Shown in FIG. 6 is an alternative embodiment of a vascular catheter 44 having a long lumen rapid exchange design. The vascular catheter 44 includes a catheter body 46 having a distal end 48 and a proximal end (not shown). The catheter body 46 has a distal region 50 and a proximal region 52. The proximal region 52 includes a guide wire lumen 54 and a working lumen 56. In communication with both the guide wire lumen 54 and the working lumen 56 is a common lumen 58. Extending through both the common lumen 58 and the guide wire lumen 54 is a guide wire 60.

The guide wire lumen 54 terminates in a channel 62 as it exits the catheter body 46 at the proximal region 52. The channel 62 extends laterally outward from a central axis of the catheter body 46 and includes a bottom surface 64 and two opposing walls 66, 68. As described in greater detail hereinafter, at least a portion of the channel 62 is curved, i.e., spiraled around the catheter body 46, to assist in preventing the guide wire 60 from wrapping itself around the catheter body 46 after exiting the channel 62. Preferably, the channel 62 has a radial cross-sectional geometry. Alternatively, the geometry can be U-shaped.

Disposed in the working lumen 56 is an ultrasonic imaging core 70. As described in greater detail hereinafter, the imaging core 70 can be advanced into the common lumen 58 after the guide wire 62 has been withdrawn from the common lumen 58 to image the region of interest.

Figure 7:
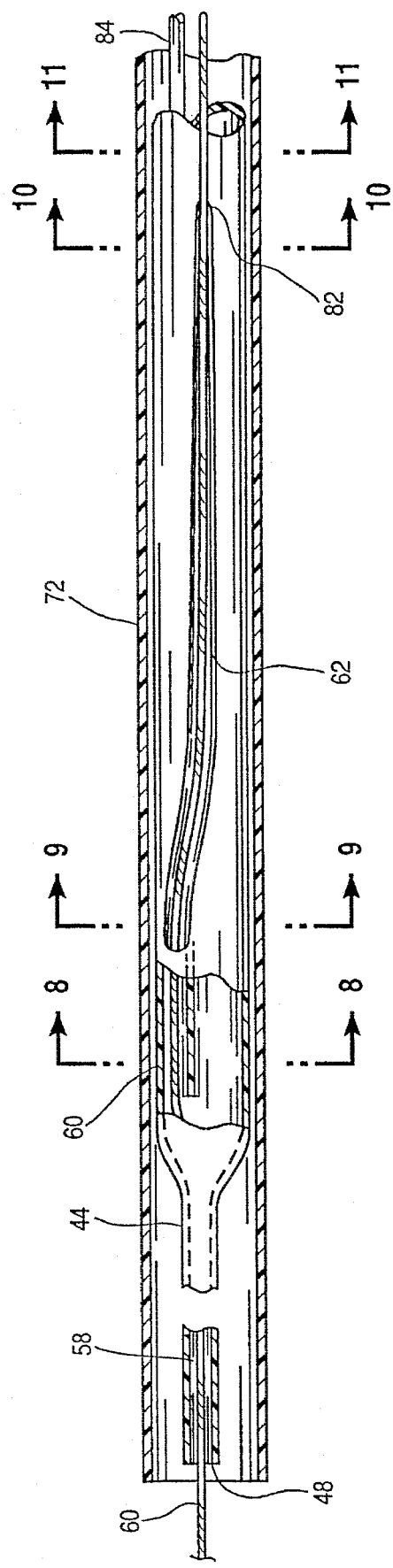
FIG. 7 illustrates the catheter of FIG. 6 disposed within a guiding catheter.

Referring to FIGS. 7–11, the vascular catheter 46 held within a guiding catheter 72 will be described in greater detail. As shown in FIG. 7, the guide wire 60 extends through the distal end 48, the common lumen 58, the guide wire lumen 60, and exits through channel 62. (Illustration of the guide wire 60 has been omitted from FIGS. 8–10 for purposes of clarity.) As best shown in FIGS. 8–11, the catheter body 46 is asymmetrical and includes two sides 74, 76, a top 77, and a bottom 78, with the dimension between the top 77 and the bottom 78 being larger than the dimension between the sides 74, 76. The channel 62 is formed in the side 76 as shown in FIGS. 9 and 10. Alternatively, the channel 62 can be formed in the side 74. As the guide wire 60 exits the guide wire lumen 54, it is preferred to have the guide wire 60 remain along the side 76 as travels the remaining length of the catheter body 46. Such a configuration allows the guide wire 60 to be maintained within a space 80 that is formed between the side 76 and the guiding catheter 72 so that the guide wire 60 will not wrap around the catheter body 46. This improves the trackability of the catheter 44.

Preferably, the channel 62 is disposed about 20 cm to 30 cm from the distal end 48, and the channel will have a length in the range from about 3 mm to 25 mm.

To help maintain the guide wire 60 within the space 80, the channel 62 is spiralled in a downward direction, i.e. toward the bottom 78. As the channel 62 reaches a proximal end 82 (see FIG. 7), the channel 62 is generally aligned with the central axis of the catheter body 46. This orients the guide wire 60 at a preferred location along the side 76 and assists in maintaining the guide wire 60 in the space 80 as it travels along the catheter body 46.

To assist in advancing the vascular catheter 44 through the guiding catheter 72, a rod 84 can be provided in a positioning lumen 86 (see FIG. 11) in the catheter body 46. The positioning lumen 86 ends just proximal to the termination of the guide wire lumen 54. Advancement of the rod 84 results in advancement of the catheter body 46 through the guiding catheter 72.

Figure 12:
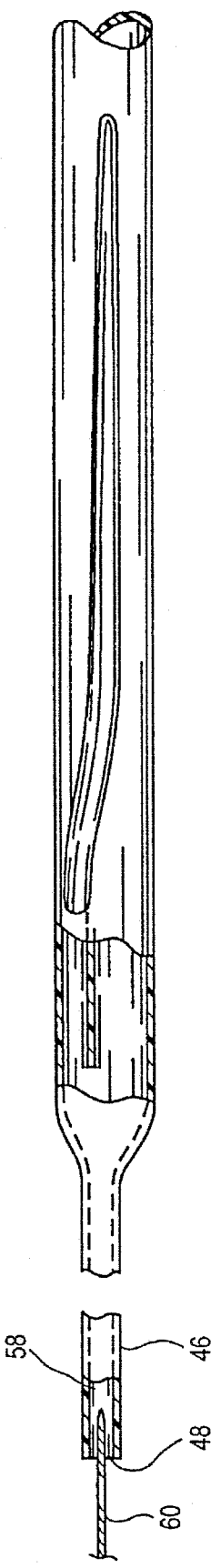
FIGS. 12–15 illustrate a method for inserting a guide wire into the catheter of FIG. 7 according to the present invention.
Figure 13:
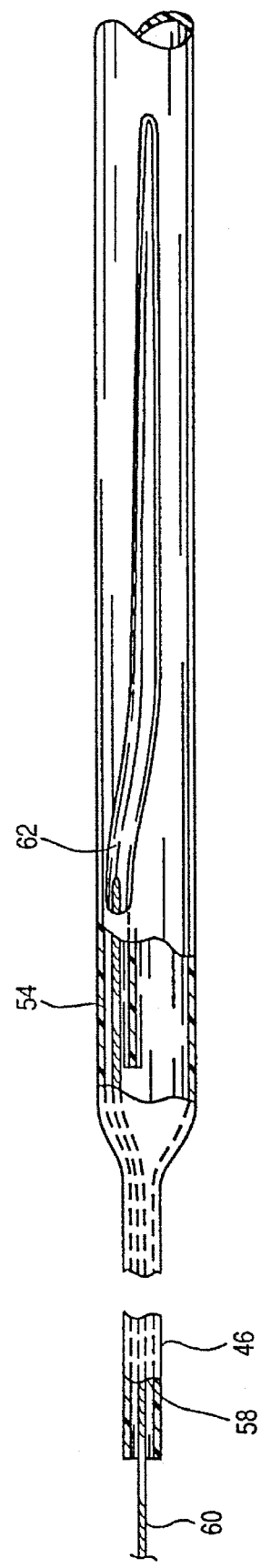

Referring to FIGS. 12–15, an exemplary method for introducing the vascular catheter 44 of FIG. 6 over the guide wire 60 and into the guiding catheter 72 will be described. Initially, the guide wire 60 is advanced through the distal end 48 of the catheter body 46 and into the common lumen 58 as shown in FIG. 12. The guide wire 60 is then further advanced through the common lumen 58 and into the guide wire lumen 54 as shown in FIG. 13. The guide wire 60 is advanced through the guide wire lumen 54 until the guide wire 60 is advanced through the catheter body 46 and into the channel 62.

Figure 14:
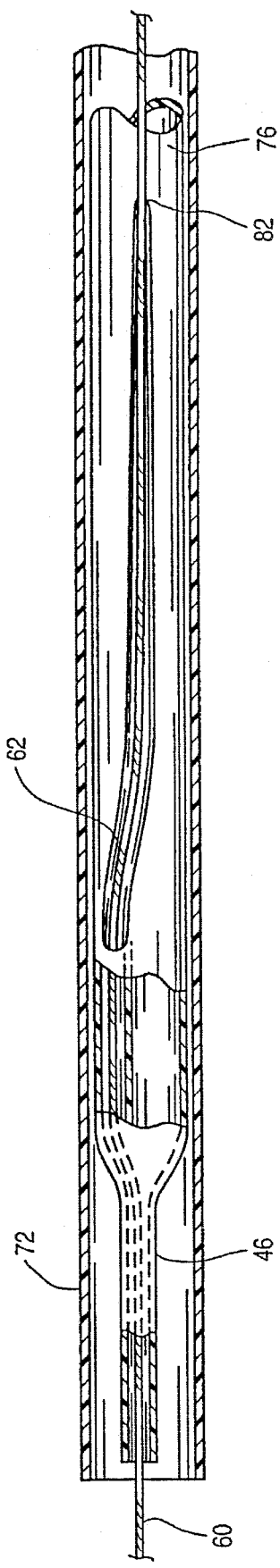

As shown in FIG. 14, the guide wire 60 is further advanced through the channel 62 until the guide wire 60 passes beyond the distal end 82 of the channel 62. As the guide wire 60 passes beyond the distal end 82, the guide wire 60 will be generally aligned with the central axis of the catheter body 46 and along the side 76. The vascular catheter 44 is then advanced over the guide wire 60 and into the guiding catheter 72. The channel 62 assists in maintaining the guide wire 60 along the side 76 as the catheter 44 is advanced into the guiding catheter 72.

Figure 15:
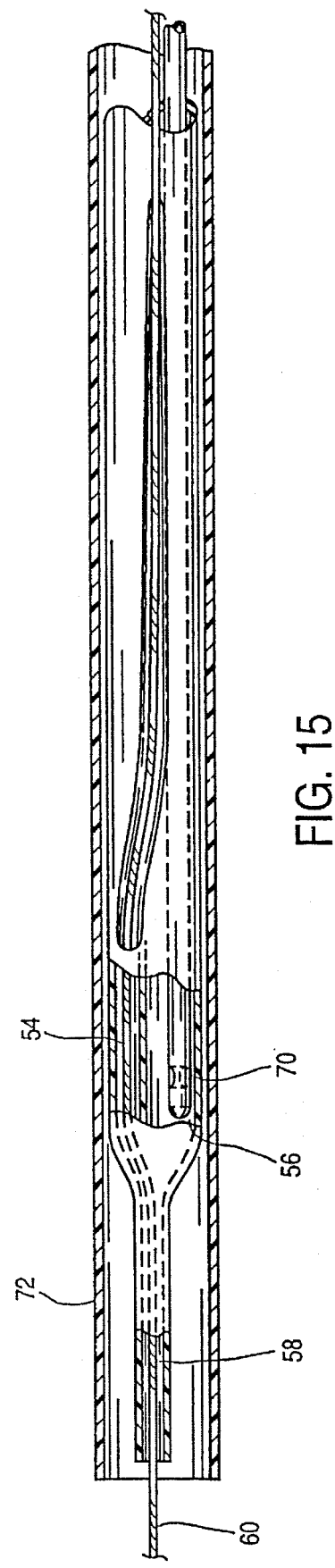

Once the vascular catheter 44 is positioned within the guiding catheter 72, the ultrasonic imaging core 70 can be introduced into the working lumen 56, as shown in FIG. 15. At this point, the guide wire 60 can be withdrawn from the common lumen 58 and into the guide wire lumen 54 so that the imaging core 70 can be advanced into the common lumen 58 where imaging can occur.

Although the foregoing invention has been described in some detail by way of illustration and example, for purposes of clarity of understanding, it will be obvious that certain changes and modifications may be practiced within the scope of the appended claims.

What is claimed is:

1. A vascular catheter, comprising:

a catheter body having a proximal end and a distal end, and a central axis therebetween; and a guide wire lumen which extends from the distal end and terminates in a channel directed laterally outward from the central axis and through the catheter body between said proximal and distal ends, wherein the channel is defined by a pair of opposing walls and a surface therebetween which is inclined radially outward from the central axis to orient a guide wire in a direction generally aligned with the central axis as it leaves the catheter body.

2. The catheter of claim 1, wherein the channel extends over a length in the range from about 3 mm to 25 mm.

3. The catheter of claim 1, wherein the channel is aligned precisely with the central axis.

4. The catheter of claim 3, wherein the crosssectional geometry of the opposing walls and the surface is U-shaped.

5. The catheter of claim 1, wherein the channel is spiralled around at least a portion of the catheter body.

6. A vascular catheter, comprising:

a catheter body having a proximal end, a distal end, and a central axis therebetween;

a central lumen generally aligned with the central axis, the central lumen extending from the proximal end and terminating near the distal end;

a guide wire lumen which extends from the distal end and terminates in a channel directed laterally outward from the central axis and through the catheter body near the termination of the central lumen, wherein the channel is defined by a pair of opposing walls and a surface therebetween which is inclined radially outward from the central axis to orient a guide wire in a direction generally aligned with the central axis as it leaves the catheter body, and wherein the channel is open to the environment over a length in the range from 3 mm to 25 mm.

7. The catheter of claim 6, wherein the surface is inclined at an angle in the range from 5 degrees to 30 degrees from the central axis.

8. The catheter of claim 6, wherein the channel is aligned precisely with the central axis.

9. The catheter of claim 6, wherein the channel is about 1.5 cm to 5 cm from the distal end.

10. A vascular catheter, comprising:

a catheter body having a proximal end and a distal end, and a central axis therebetween, wherein the catheter body includes a proximal region having at least two lumens and a distal region having a single lumen which is connected to and in communication with both of the lumens in the proximal region and having a cross-sectional area which is less than the combined cross-sectional area of the two lumens of the proximal region; and wherein one of the lumens in the proximal region is a guide wire lumen which extends from the single lumen and which terminates in a channel directed laterally outward from the central axis and through the catheter body between the proximal end and the single lumen, wherein the channel is defined by a pair of opposing walls and a surface therebetween which is inclined radially outward from the central axis to orient a guide wire in a direction generally aligned with the central axis as it leaves the catheter body.

11. The catheter of claim 10, wherein the catheter body at the proximal region has two sides, a top, and a bottom, wherein the top-to-bottom dimension is larger than the side-to-side dimension, and the channel is directed to align the guide wire along one of the sides.

12. The catheter of claim 11, wherein a portion of the channel is spiralled about the catheter body to align a guide wire along the side having the channel.

13. The catheter of claim 12, wherein one of the lumens in the proximal region is a working lumen and is disposed between the guide wire lumen and the bottom.

14. The catheter of claim 10, wherein the distal region has a length in the range from 10 cm to 20 cm, and wherein the channel is disposed near a proximal end of the distal region.

15. The catheter of claim 10, wherein the channel is about 20 cm to 30 cm from the distal end.

16. A method for introducing a vascular catheter into an access lumen of a guiding catheter, the vascular catheter having a proximal end, a distal end, and a central axis therebetween, the method comprising:

inserting a guide wire into the access lumen of the guiding catheter;

inserting a proximal end of the guide wire into a lumen of the vascular catheter;

proximally advancing the vascular catheter over the guide wire so that the proximal end of the guide wire exits the vascular catheter along a side of the vascular catheter and passes through a channel in the side of the vascular catheter, wherein the channel is defined by a pair of opposing walls and a surface therebetween which is inclined radially outward from the central axiS, wherein the channel orients the guide wire along the side of the vascular catheter in a direction generally aligned with the central axis.

17. The method of claim 16, wherein the vascular catheter includes a central lumen disposed between the guide wire lumen and a bottom edge of the vascular catheter, and wherein the channel is at least partially curved and orients the exit of the guide wire from the guide wire lumen toward the bottom edge and then along the side of the vascular catheter in a direction generally aligned with the central axis.

18. The method of claim 17, further comprising introducing imaging catheter into the central lumen.

19. The method of claim 16, wherein the guide wire passes through the channel at an angle from 5 degrees to 30 degrees from the central axis.

* * * * *